United States Patent [19]

Fahey

[11] 4,101,566
[45] Jul. 18, 1978

[54] OXIDATIVE ADDITION PRODUCTION OF TRANS-HALO-2(1,3-ALKADIENYL)BIS(-TRIETHYLPHOSPHINE) COMPLEXES OF NICKEL(II), PALLADIUM(II), AND PLATINUM(II)

[75] Inventor: Darryl R. Fahey, Bartlesville, Okla.

[73] Assignee: Phillips Petroleum Company, Bartlesville, Okla.

[21] Appl. No.: 739,762

[22] Filed: Nov. 8, 1976

[51] Int. Cl.$^2$ .................. C07F 15/00; C07F 15/04
[52] U.S. Cl. ........................... 260/439 R; 260/429 R
[58] Field of Search ...................... 260/429 R, 439 R

[56] References Cited

U.S. PATENT DOCUMENTS

| 3,194,848 | 7/1965 | Feldman et al. | 260/666 |
| 3,674,825 | 7/1972 | Fitton et al. | 260/429 R |
| 3,686,245 | 8/1972 | Fahey | 260/439 R |
| 3,808,246 | 4/1974 | Fahey | 260/439 R |

OTHER PUBLICATIONS

Parshall, JACS 96, 2360, (1974).
Collman et al., Inorganic Chem. 8, 2574–2579, (1969).
Fahey, JACS 92, 402–404, (1970).
Kramer, JACS 96, 7832–7833, (1974).
Gerlach et al., JACS 93, 3543–3544, (1971).
Green et al., J. Chem. Soc. (A), 2525–2530, (1966).
Hidai et al., J. Organometal. Chem. 30, 279–282, (1971).
Kramer et al., JACS 96, 7145–7147, (1974).
Belluco, Organometallic and Coordination Chemistry of Platinum, Academic Press, N.Y., pp. 3, 4, 96–100, (1974).
Maitlis, The Organic Chemistry of Palladium, Academic Press, N.Y., pp. 21–23, (1971).
Malatesta et al., Zerovalent Compounds of Metals, Academic Press, N.Y., pp. 106–111 (1974).
Collman, Advances in Organometallic Chemistry, 7, 75–77, (1968).

Primary Examiner—Helen M. S. Sneed

[57] ABSTRACT

The production of trans-halo-2(1,3-alkadienyl)bis(triethylphosphine) complexes of nickel(II), palladium(II), and platinum(II) by oxidative addition is disclosed.

15 Claims, No Drawings

OXIDATIVE ADDITION PRODUCTION OF TRANS-HALO-2(1,3-ALKADIENYL)BIS(TRIETHYLPHOSPHINE) COMPLEXES OF NICKEL(II), PALLADIUM(II), AND PLATINUM(II)

This invention relates to the production of trans-halo-2(1,3-alkadienyl)bis(triethylphosphine) complexes of nickel(II), palladium(II), and platinum(II).

The oxidative-addition reaction of organic halides with certain zero-valent nickel, palladium, and platinum complexes has been used as a route for obtaining the corresponding trans-halo-(organo)bis(triorganophosphine) metal(II) complexes. For example, the *Journal of the American Chemical Society*, 92(2), 402 (1970), discloses the preparation of trans-chloro(trifluorovinyl)bis(triethylphosphine)nickel(II) and trans-chloro-(trichlorovinyl)bis(triethylphosphine)nickel(II) by the oxidative-addition of chlorotrifluoroethylene or tetrachloroethylene, respectively, to (ethylene)bis(triethylphosphine)nickel(O).

In attempting to prepare trans-halo-2(1,3-alkadienyl)bis(triorganophosphine) complexes of nickel(II), palladium(II), or platinum(II) by the oxidative-addition of haloprenes to zero-valent nickel, palladium, or platinum complexes, it was discovered that the reaction would work only if certain zero-valent metal complexes were employed.

Accordingly, an object of this invention is to provide a method for preparing trans-halo-2(1,3-alkadienyl)bis(triethylphosphine) complexes of nickel(II), palladium(II) or platinum(II) by the oxidative addition of haloprenes to certain zero-valent nickel, palladium, or platinum complexes.

Other aspects, objects, and advantages of this invention will be apparent to one skilled in the art from this disclosure and the appended claims.

According to the present invention a trans-halo-2(1,3-alkadienyl)bis(triethylphosphine) metal(II) complex is produced having the following formula:

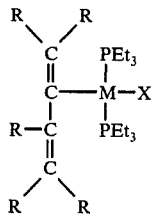

wherein X is chlorine, bromine, or iodine; four R groups are hydrogen and the remaining R group is hydrogen or methyl; M is nickel(II), palladium(II), or platinum(II); and PEt$_3$ represents triethylphosphine. The process for producing such a complex involves contacting in solution a haloprene of the formula

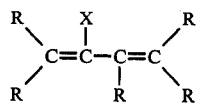

wherein R and X are as defined above, and a zero-valent complex having the formula M(PEt$_3$)$_n$ or M(1,5-COD)(PEt$_3$)$_2$ wherein M and PEt$_3$ are as defined above, n is 3 or 4, and 1,5-COD represents 1,5-cyclooctadiene, under conditions suitable for producing the corresponding trans-halo-2(1,3-alkadienyl)bis(triethylphosphine) metal(II) complex. It is considered that the 1,3-alkadienyl metal(II) complexes produced according to this invention would be effective catalyst components for the oligomerization of olefins. For example, the nickel metal complexes produced according to this invention can be employed in catalyst systems for the dimerization of olefins in accordance with the disclosure in Ernest Zuech's U.S. Pat. No. 3,485,881. Also, it is considered that the 1,3-alkadienyl metal(II) complexes produced according to this invention could be substituted for similar nickel, palladium, or platinum complexes in other known catalytic processes.

Examples of haloprenes suitable for use in this invention include chloroprene, bromoprene, iodoprene, 3-methyl-2-chloro-1,3-butadiene, 2-bromo-1,3-pentadiene, and 3-chloro-1,3-pentadiene. The haloprene can be produced employing techniques known to those skilled in the art. Those skilled in the art will recognize that some haloprenes, i.e., 2-halo-1,3-alkadienes, viz., chloroprene, are generally supplied commercially in the form of a xylene solution. Although such solutions can be used in the present process, it is preferred that such a solution of haloprene not be employed directly in the oxidative addition reaction of this invention because such commercial solutions generally contain polymerization inhibitors which might interfere with the desired reaction. Of course such commercially available solutions can be preferably distilled to yield haloprene which is sufficiently pure for use in the present invention.

The metal complexes employed and prepared in accordance with this invention are sensitive to oxygen and/or water to varying degrees. Therefore, the preparation and use of these complexes should be under an inert atmosphere, for example, in a recirculating atmosphere dry box providing a suitable inert atmosphere, for example, argon.

In this invention any solvent can be employed which does not prevent the formation of the desired product. The amount of solvent needed is generally that amount which will insure that a sufficient amount of the reactants is in the liquid phase at the reaction temperature to yield the desired product. One skilled in the art having the benefit of this disclosure can readily vary the concentrations of reactants and to obtain different reaction rates and yields of product. Examples of suitable solvents include suitable aliphatic hydrocarbons, aromatic hydrocarbons, hydrocarbyl ethers, aliphatic nitriles, aliphatic ketones, alkyl esters of aliphatic acids, and mixtures of any two or more thereof. Typical examples of solvents include hexane, heptane, cyclohexane, octane, benzene, toluene, xylenes, dioxane, diethyl ether, tetrahydrofuran, diethylene glycol dimethyl ether, acetonitrile, propionitrile, butyronitrile, acetone, methylethyl ketone, diethyl ketone, methyl acetate, ethyl acetate, methyl propionate, and mixtures of any two or more thereof.

While any temperatures can be employed which are suitable for the oxidative addition reaction, generally the haloprene and zero-valent metal complex are contacted in the temperature range of −30° C. to about 100° C., preferably about 0° C. to about 40° C. Likewise any pressure suitable for the oxidative addition reaction can be employed. The pressure employed is generally that at which the reaction mass will essentially be in the liquid phase at the reaction temperature, preferably the reaction is conducted at atmospheric pressure. The time for the reaction is that necessary for the oxidative addition reaction. Generally the reaction time is in the range of about one minute to five hours, preferably in the range of 2 minutes to 30 minutes. Also while any molar ratios can be employed which are suitable for the oxidative addition reaction, generally the molar ratio of the zero-valent metal complex to the haloprene is in the range of about 1:5 to about 5:1, preferably about 1:2 to about 1:1.

The zero-valent complexes of the formula M(PEt$_3$)$_n$, as above defined, and the (1,5-cyclooctadiene)bis(triethylphosphine)metal(O) complexes, as defined above, can be prepared in any suitable manner known in the art. A preferred embodiment of the present invention involves utilizing the product mixture which results when a zero-valent nickel, palladium, or platinum bis(1,5-cyclooctadiene) complex and triethylphosphine in a molar ratio of about 4:1 to about 2:1, preferably about 3:1 to 2:1, are contacted in a suitable solvent. In preparing this product mixture which is subsequently contacted preferably with a solution of haloprene, any solvent can be employed which does not adversely affect the inventive process. Examples of suitable solvents include those set forth above for the inventive oxidative addition process. While higher or lower temperatures can be employed, generally the temperature at which the (1,5-cyclooctadiene)bis(triethylphosphine)metal(O) complex is produced in this manner is in the range of −30° C. to about 100° C., preferably about 0° C. to about 40° C. Here again the pressure employed is generally that which will essentially maintain the reaction mass in the liquid phase at the temperatures employed. Of course, it is very convenient to conduct this reaction at atmospheric pressure.

The products of the present invention can be recovered by any suitable techniques conventionally employed by those skilled in the art for recovering and purifying products contained in a diluent or solvent, i.e., precipitation followed by filtration, or extraction; evaporation to dryness in vacuo, or separation of impurities by elution column chromatography followed by recrystallization. It is thus convenient if the solvent employed is one in which the product is relatively insoluble at a temperature of about −20° C. to about −80° C. so that product can be recovered by precipitation, or alternatively, if the solvent is sufficiently volatile that the product can be isolated by solvent evaporation at a temperature which does not adversely affect the product.

The following examples are provided to further illustrate the present invention and to demonstrate that it is unexpected that the process does produce the trans-halo-2(1,3-alkadienyl)bis(triethylphosphine)metal(II) complexes. Each of these examples was conducted in a dry box maintained at atmospheric pressure. The dry box provided a recirculating atmosphere of argon.

EXAMPLE I

A 50 ml Erlenmeyer flask equipped with a magnetic stirring bar was placed in a dry box and charged with 5.5 g (20 mmols) of bis(1,5-cyclooctadiene)nickel(O), 4.8 g (40 mmols) of triethylphosphine and 20 ml of ethyl ether. The reaction components were thoroughly mixed and cooled to −70° C. At this point the solution was dark and appeared to contain some undissolved bis(1,5-cyclooctadiene)nickel(O). After the addition of 2.0 g (23 mmols) of 2-chloro-1,3-butadiene, the stirred mixture was warmed to 25° C. and then recooled to −70° C. at which temperature large crystals formed. The reaction mixture was allowed to stand at 25° C. for about 14 hours. Product recovery was effected by diluting the reaction mixture with 5 ml of hexane and cooling to −70° C. The yellow-brown crystals which formed were recovered by suction filtration to give 2.94 g (38 percent yield) of trans-chloro-2(1,3-butadienyl)bis(triethylphosphine)nickel(II), m.p. 68°–68.5° C. Structure verification of this product was based on its infrared spectrum which was identical to that of a sample of authentic trans-chloro-2(1,3-butadienyl)bis(triethylphosphine)nickel(II), m.p. 66°–67.5° C., prepared from a Grignard reagent according to the method disclosed in U.S. Pat. No. 3,485,881, column 3, lines 9–20. Additional product was obtained from the above filtrate to give a total of 6.3 g (83 percent yield) of trans-chloro-2(1,3-butadienyl)bis(triethylphosphine)nickel(II).

EXAMPLE II

A 125 ml Erlenmeyer flask equipped with a magnetic stirring bar was placed in a dry box and charged with 0.55 g (2.0 mmols) of bis(1,5-cyclooctadiene)nickel(O), 1.05 g (4.0 mmols) of triphenylphosphine and 5 ml of benzene. The reaction components were thoroughly mixed and cooled to 5°–10° C. Then 0.20 g (2.3 mmols) of 2-chloro-1,3-butadiene was added and the stirred solution was maintained at about 5°–10° C. after one hour, hexane was added and a yellow solid began to precipitate. After an additional 1–2 hours, the yellow solid was recovered by suction filtration, washed with a mixture of benzene-hexane and dried to a weight of 0.48 g. The infrared spectrum of this product did not exhibit characteristic absorption peaks for the 2(1,3-butadienyl) moiety which would have been exhibited by trans-chloro-2(1,3-butadienyl)bis(triphenylphosphine)nickel(II).

This example illustrates that 2-chloro-1,3-butadiene does not undergo the desired oxidative addition reaction in the product mixture that results when bis(1,5-cyclooctadiene)nickel(O) and triphenylphosphine are contacted in amounts such that the molar ratio of nickel to triphenylphosphine is 1:2 and the molar ratio of nickel to 2-chloro-1,3-butadiene is 0.87:1. Since the analogous molar ratios were essentially the same as those of Example I, this example indicates that the choice of triorganophosphine is critical.

EXAMPLE III

A 125 ml Erlenmeyer flask equipped with a magnetic stirring bar was placed in a dry box and charged with 0.55 g (2.0 mmols) of bis(1,5-cyclooctadiene)nickel(O), 0.52 g (2.0 mmols) of triphenylphosphine and 15 ml of benzene. The solution was cooled to about 5° C. and 0.20 g (2.3 mmols) of 2-chloro-1,3-butadiene was added. After one hour, some black solid had precipitated and was collected by suction filtration. An infrared spectrum of this material showed no 2(1,3-butadienyl) absorption bands. The spectrum showed only triphenylphosphine and triphenylphosphine oxide absorption bands.

The filtrate from above was evaporated to dryness in vacuo and the residue was extracted with hexane. The hexane extract was filtered and the filtrate was cooled to 5° C. but no crystallization occurred.

This example illustrates that 2-chloro-1,3-butadiene does not undergo the desired oxidative addition in the product mixture that results when bis(1,5-cyclooctadiene)nickel(O) is contacted with triphenylphosphine in such amounts that the molar ratio of triphenylphosphine to nickel is 1:1 and the molar ratio of nickel to 2-chloro-1,3-butadiene is 0.87:1.

EXAMPLE IV

A small glass vessel equipped with a magnetic stirring bar was placed in a dry box and charged with 1.10 g (4.0 mmols) of bis(1,5-cyclooctadiene)nickel(O), 10.4 g (4.0 mmols) of triphenylphosphine and 20 ml of ethyl ether. This mixture was chilled to −60° C. and a yellow precipitate and a dark brown solid formed. After the addition of 0.4 g (4.5 mmols) of 2-chloro-1,3-butadiene to the cold mixture, stirring was continued for 1–2 hours with no further change in the appearance of the reaction mixture. On warming to ambient temperature, the solution turned brown and a brown solid was deposited. No tractable solid products were obtained from the brown precipitate or from the filtrate.

This example illustrates that 2-chloro-1,3-butadiene does not undergo the desired oxidative addition reaction in the product mixture which results when bis(1,5-cyclooctadiene)nickel(O) complex is contacted with triphenylphosphine in such amounts that the molar ratio of nickel to triphenylphosphine is 1:1 and the molar ratio of nickel to 2-chloro-1,3-butadiene is 0.89:1.

Examples III and IV provide further support that the choice of triorganophosphine is critical to achieving the desired oxidative addition reaction.

EXAMPLE V

A 50 ml Erlenmeyer flask equipped with a magnetic stirring bar was placed in a dry box and charged with 1.38 g (5 mmols) of bis(1,5-cyclooctadiene)nickel(O), 0.60 g (5 mmols) of triethylphosphine and 35 ml of benzene. The reaction components were thoroughly mixed and cooled to about 0° C. After the addition of 0.5 g (5.8 mmols) of 2-chloro-1,3-butadiene, a small amount of dark red-brown solid precipitated. An infrared spectrum of this solid did not exhibit the absorption bands characteristic of the 2(1,3-butadienyl) grouping. A portion of the filtrate was evaporated to dryness to give additional brown solid with an infrared spectrum identical to that above.

The mushy dark reaction product was dissolved in benzene and contacted with alumina. The sample was eluted with acetonitrile, concentrated to a red oil and examined by infrared spectroscopy. This hexane-insoluble red oil did not exhibit the absorption bands characteristic of the 2(1,3-butadienyl) moiety. Nuclear magnetic resonance analysis of the red oil showed the major component to be triethylphosphine.

No crystallization occurred in the cold from a mixture of the red oil in acetonitrile diluted with hexane and ether.

This example demonstrates that 2-chloro-1,3-butadiene does not undergo the desired oxidative addition reaction in the product mixture which results when bis(1,5-cyclooctadiene)nickel(O) is contacted with triethylphosphine in such amounts that the molar ratio of nickel to triethylphosphine is 1:1 and the molar ratio of nickel to 2-chloro-1,3-butadiene is 0.86:1.

This example when compared with Example I indicates that when the haloprene is reacted with the product mixture resulting from a reaction of $PEt_3$ and 1,5-COD, the molar ratio of triethylphosphine to bis(1,5-cyclooctadiene)nickel can affect the production of the desired metal(II) compound.

EXAMPLE VI

A small glass vessel equipped with a magnetic stirring bar was placed in a dry box and charged with 1.38 g (5.0 mmols) of bis(1,5-cyclooctadiene)nickel(O), 50 ml of tetrahydrofuran and chilled to about −20° C. A 1.40 g (5 mmols) sample of tricyclohexylphosphine was added followed by dropwise addition of 0.5 g (5.8 mmols) of 2-chloro-1,3-butadiene to the rapidly stirred reaction mixture. After warming the solution to ambient temperature, a brown solid was removed by filtration. The infrared spectrum of this solid exhibited the absorption bands characteristic of tricyclohexylphosphine. No crystalline nickel-containing compounds were recovered from the filtrate.

This example illustrates that 2-chloro-1,3-butadiene does not undergo the desired oxidative addition reaction in the product mixture that results when bis(1,5-cyclooctadiene)nickel(O) is contacted with tricyclohexylphosphine in such amounts that the molar ratio of nickel to added tricyclohexylphosphine is 1:1 and the molar ratio of nickel to 2-chloro-1,3-butadiene is 0.86:1.

This example can be viewed as indicating that either (1) the choice of trioganophosphine or (2) the molar ratio of triorganophosphine to nickel complex is critical to achieving the desired oxidative addition reaction.

EXAMPLE VII

A small glass vial was placed in a dry box, charged with 1.14 g (1.97 mmols) of tetrakis(triethylphosphine)palladium(O) and subjected to high vacuum (~0.5 mm Hg) for 3 hours at ambient temperature. The sample gave up 0.34 g (2.9 mmols) of triethylphosphine leaving a residue of 0.8 g (1.74 mmols) of tris(triethylphosphine)palladium(O). This residue was dissolved in 2 ml of hexane and added in a dropwise fashion to a stirred solution of 0.2 g (2.3 mmols) of 2-chloro-1,3-butadiene in 5 ml of hexane. After stirring this solution at 25° C. it was stored at −30° C. for about 14 hours. The solution was taken to dryness in vacuo and this residue was further subjected to vacuum to remove some additional triethylphosphine which would interfere with product recovery because of its oily nature. The residue was then dissolved in hexane and recrystallized at −72° C. to give 0.56 g (75 percent yield) of trans-chloro-2(1,3-butadienyl)bis(triethylphosphine)palladium(II) as a yellow solid melting at 59°–64° C. The product was further purified by an additional recrystallization from hexane to give 0.46 g (61 percent yield) of product melting at 64°–66° C.

|  | Elemental Analysis: | |
|---|---|---|
|  | % C | % H |
| Theoretical | 44.56 | 8.18 |
| Found | 44.47 | 8.22 |

EXAMPLE VIII

A small glass vial was placed in a dry box and charged with 0.66 g (1.53 mmols) of tetrakis(triethylphosphine)palladium(O), 8 ml of hexane and approximately 0.5 g. (ca. 6 mmols) of 2-chloro-1,3-butadiene. The solution was allowed to stand at −30° C. for about 64 hours. The mixture was concentrated in vacuo to a yellow oil which on trituration with about 3 ml of hexane and subsequent cooling to −72° C. resulted in the isolation of 0.08 g (12 percent yield, m.p. 57°–61° C.) of trans-chloro-2(1,3-butadienyl)bis(triethylphosphine)-palladium(II).

The following three examples employ zero-valent complexes that differ from $M(PEt_3)_n$, as defined above in that they have different triorganophosphine ligands. These examples demonstrate the unexpectedness of the oxidative addition reaction which occurs on employing a zero-valent complex of the formula $M(PEt_3)_n$ as defined above.

EXAMPLE IX

A small glass vessel equipped with a magnetic stirring bar was placed in a dry box and charged with a mixture of 2.31 g (2.0 mmols) of tetrakis(triphenylphosphine)-palladium(O) and 20 ml of benzene at ambient temperature. A 0.18 g (2.0 mmols) sample of 2-chloro-1,3-butadiene was added and stirring was continued at ambient temperature. In order to solubilize all the components, the reaction mixture was stirred at 60°–70° C., and during a period of about seven days, heating and stirring was continued as small amounts of 2-chloro-1,3-butadiene were intermittently added. At the end of seven days, the reaction mixture was cooled to ambient temperature and the only solid product isolated was tetrakis(triphenylphosphine)palladium(O) (verified by infrared spectral analysis).

EXAMPLE X

A 125 ml Erlenmeyer flask equipped with a magnetic stirring bar was placed in a dry box and charged with 1.11 g (1.0 mmol) of tetrakis(triphenylphosphine)nickel(O) and 6 ml of benzene. A 0.20 g (2.3 mmols) sample of triply distilled 2-chloro-1,3-butadiene was added to the stirred reaction mixture and the reaction vessel was stoppered with an appropriate cork. Yellow crystals began to precipitate and the mixture was allowed to stand at ambient temperature for about 14 hours.

After cooling the reaction mixture for 2 hours at about 5°–10° C., the fluffy yellow crystals were removed by suction filtration, washed with a mixture of benzene-hexane and dried to a weight of 0.52 g. This product melted at 160°–162° C. which corresponds to the melting point exhibited by an authentic sample of a benzene solvate of chloro-tris(triphenylphosphine)nickel(I) prepared by a different technique.

EXAMPLE XI

A small glass vessel equipped with a magnetic stirring bar was placed in a dry box and charged with 0.56 g (2.0 mmols) of bis(1,5-cyclooctadiene)nickel(O) and 5 ml of benzene. Approximately 0.13 g (1.5 mmols) of triply distilled 2-chloro-1,3-butadiene was added and almost immediately a black precipitate of elemental nickel and a nickel mirror appeared. This was viewed as an indication that there was no production of any organometallic nickel complexes.

EXAMPLE XII

An oven dried 9 ounce glass bottle reactor equipped with a magnetic stirring bar was charged with 0.038 g (0.10 mmol) of trans-chloro-2(1,3-butadienyl)bis(triethylphosphine)nickel(II) and 20 ml of redistilled chlorobenzene. After flushing the system with nitrogen and propylene, the capped glass bottle reactor was cooled in an ice salt bath for 5 minutes and then pressured to 30 psig with propylene. The glass bottle reactor was vented to 5 psig and 0.70 ml of a 1 M solution of methylaluminum sesquichloride in chlorobenzene [0.70 mmol $(CH_3)_3Al_2Cl_3$] was added by means of a syringe. The bottle reactor was pressured with propylene to 30 psig and by the addition of propylene as necessary was maintained at this pressure in the cold bath for a period of about 53 minutes. At this point the bottle reactor was nearly liquid full and the introduction of propylene was stopped. The bottle was vented and 10 ml of saturated aqueous sodium chloride was added. The organic and aqueous phases were separated and the aqueous phase was extracted with 5 ml of chlorobenzene. The organic phases were combined, dried over anhydrous magnesium sulfate and distilled to give a 91.7 g fraction of mixed hexene isomers as a colorless liquid boiling over the range of 58.6°–68° C.

A 2.0 g sample of the above product was hydrogenated over 0.1 g $PtO_2$ under 20 psi hydrogen for a period of 3¼ hours. Examination of the hydrogenated material by glpc on a 20′ isoquinoline column at 25° C. gave the following analysis:

| Components | Area Percent |
| --- | --- |
| 3,3-dimethylbutane | 23.3 |
| 2-methylpentane | 68.2 |
| n-hexane | 8.4 |

This example illustrates how the metal (II) complexes of this invention can be employed in catalyst systems for the dimerization of olefins in accordance with the previously mentioned U.S. Pat. No. 3,485,881.

It is to be noted that the nomenclature "trans-halo-2(1,3-alkadienyl)bis(triethylphosphine) complex" used throughout this disclosure is intended to denote the same chemical species that would be known under the nomenclature "trans-halo(1,3-alkadien-2-yl)bis(triethylphosphine) complex".

What is claimed is:

1. A process comprising contacting in solution a haloprene of the formula

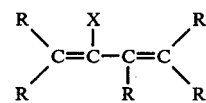

wherein X is chlorine, bromine, or iodine, four R groups are hydrogen and the remaining R group is hydrogen or methyl, and a zero valent complex having the formula

wherein M is nickel, palladium, or platinum, $PEt_3$ represents triethylphosphine, n is 3 or 4, or

wherein M and $PEt_3$ are as defined above and 1,5-COD represents 1,5-cyclooctadiene, under conditions suitable for producing the corresponding trans-halo-2(1,3-alkadienyl)bis(triethylphosphine) metal(II) complex of the formula

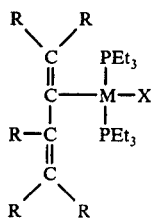

wherein M, X, R, and PEt₃ are as defined above.

2. A process according to claim 1 wherein said zerovalent complex is employed in the form of the product mixture that results when triethylphosphine and a bis(1,5-cyclooctadiene)metal(O) complex of nickel, palladium, or platinum are contacted in solution in amounts such that the molar ratio of triethylphosphine to said bis(1,5-cyclooctadiene)metal(O) complex is in the range of about 4:1 to about 2:1 under conditions such that the corresponding (1,5-cyclooctadiene)bis(triethylphosphine)metal(O) complex is produced.

3. A process according to claim 2 wherein said bis(1,5-cyclooctadiene)metal(O) complex is bis(1,5-cyclooctadiene)nickel(O).

4. A process according to claim 3 wherein the amount of haloprene employed is such that the molar ratio of (1,5-cyclooctadiene)bis(triethylphosphine) nickel(O) to said haloprene is in the range of about 1:5 to about 5:1.

5. A process according to claim 4 wherein the amounts of triethylphosphine and bis(1,5-cyclooctadiene)nickel(O) employed in preparing the (1,5-cyclooctadiene)bis(triethylphosphine)nickel(O) are such that the molar ratio of the former to the latter is in the range of about 3:1 to about 2:1 and wherein the amount of haloprene employed is such that the molar ratio of (1,5-cyclooctadiene)bis(triethylphosphine)nickel(O) to said haloprene is in the range of about 1:2 to about 1:1.

6. A process according to claim 5 wherein the nickel complex trans-halo-2(1,3-alkadienyl)bis(triethylphosphine)nickel(II) is produced in a solution at a temperature in the range of about −30° C. to about 100° C.

7. A process according to claim 6 wherein the molar ratio of triethylphosphine to bis(1,5-cyclooctadiene)nickel(O) is about 2:1, the triethylphosphine and bis(1,5-cyclooctadiene)nickel(O) are contacted in ethyl ether at a temperature of about 25° C. to yield a product mixture; 2-chloro-1,3-butadiene in a molar amount about equal to that of the bis(1,5-cyclooctadiene)nickel(O) is added to said product mixture to about 25° C. to produce trans-chloro-2(1,3-butadienyl)bis(triethylphosphine)nickel(II).

8. A process according to claim 7 wherein the trans-chloro-2(1,3-butadienyl)bis(triethylphosphine)nickel(II) is recovered by crystallization from the solution.

9. A process according to claim 1 wherein said zerovalent complex is (1,5-cyclooctadiene)bis(triethylphosphine)nickel(O).

10. A process according to claim 1 wherein said zerovalent complex is tris(triethylphosphine)palladium(O).

11. A process according to claim 10 wherein the trans-halo-2(1,3-alkadienyl)bis(triethylphosphine)palladium(II) complex is produced in a solution at a temperature in the range of about −30° C. to about 100° C.

12. A process according to claim 11 wherein tris(triethylphosphine) palladium(O) and 2-chloro-1,3-butadiene are contacted in solution at about 25° C. to produce trans-chloro-2(1,3-butadienyl)bis(triethylphosphine)-palladium(II).

13. A process according to claim 1 wherein said zerovalent complex is tetrakis(triethylphosphine)palladium.

14. A process according to claim 13 wherein the trans-halo-2(1,3-alkadienyl)bis(triethylphosphine)palladium(II) complex is produced in a solution having a temperature in the range of about −30° C. to about 100° C.

15. A process according to claim 14 wherein tetrakis(triethylphosphine)palladium(O) and 2-chloro-1,3-butadiene are contacted in solution at about 25° C. to produce trans-chloro-2(1,3-butadienyl)bis(triethylphosphine)-palladium(II).

* * * * *